(12) United States Patent
Bendall et al.

(10) Patent No.: US 10,041,949 B2
(45) Date of Patent: Aug. 7, 2018

(54) MULTIPLEXED IMAGING OF TISSUES USING MASS TAGS AND SECONDARY ION MASS SPECTROMETRY

(71) Applicant: The Board of Trustees of the Leland Stanford Junior University, Palo Alto, CA (US)

(72) Inventors: Sean C. Bendall, San Mateo, CA (US); Garry P. Nolan, Redwood City, CA (US); Robert M. Angelo, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 321 days.

(21) Appl. No.: 14/483,999

(22) Filed: Sep. 11, 2014

(65) Prior Publication Data
US 2015/0080233 A1   Mar. 19, 2015

Related U.S. Application Data

(60) Provisional application No. 61/877,733, filed on Sep. 13, 2013, provisional application No. 61/970,803, filed on Mar. 26, 2014.

(51) Int. Cl.
*G01N 33/48* (2006.01)
*G01N 33/50* (2006.01)
(Continued)

(52) U.S. Cl.
CPC ............. *G01N 33/58* (2013.01); *G01N 15/10* (2013.01); *G01N 33/483* (2013.01);
(Continued)

(58) Field of Classification Search
None
See application file for complete search history.

(56) References Cited

U.S. PATENT DOCUMENTS

| 6,291,820 | B1 | 9/2001 | Hamza et al. |
| 6,534,764 | B1 | 3/2003 | Verentchikov et al. |

(Continued)

FOREIGN PATENT DOCUMENTS

| WO | 2000068434 A2 | 1/2002 |
| WO | 2009156725 A2 | 12/2009 |

(Continued)

OTHER PUBLICATIONS

Bodenmiller et al. Multiplexed mass cytometry profiling of cellular states perturbed by small-molecule regulators. Nature Biotechnology, vol. 30, Aug. 23, 2012, pp. 858-867 with extra protocol pages.*

(Continued)

*Primary Examiner* — Russell S Negin
(74) *Attorney, Agent, or Firm* — James S. Keddie; Bozicevic, Field & Francis LLP

(57) ABSTRACT

A method of generating a high resolution two-dimensional image of a sample comprising cells and extracellular structures is provided. In certain embodiments, the method comprises: labeling a sample with at least one mass tag, thereby producing a labeled sample; scanning the sample with a secondary ion mass spectrometer (SIMS) ion beam to generate a data set that comprises spatially-addressable measurements of the abundance of the mass tag across an area of the sample; and outputting the data set. In many embodiments, the data set contains the identity and abundance of the mass tag. A system for performing the method is also provided.

19 Claims, 5 Drawing Sheets
(5 of 5 Drawing Sheet(s) Filed in Color)

(51) Int. Cl.
*G01N 33/58* (2006.01)
*H01J 49/00* (2006.01)
*G01N 33/68* (2006.01)
*G01N 33/483* (2006.01)
*G01N 33/487* (2006.01)
*G01N 15/10* (2006.01)

(52) U.S. Cl.
CPC ... *G01N 33/48735* (2013.01); *G01N 33/5005* (2013.01); *G01N 33/6848* (2013.01); *H01J 49/0004* (2013.01); *G01N 2015/1006* (2013.01); *G01N 2458/15* (2013.01)

(56) References Cited

U.S. PATENT DOCUMENTS

| | | |
|---|---|---|
| 6,627,877 B1 | 9/2003 | Davis et al. |
| 6,849,848 B2 | 2/2005 | Baranov et al. |
| 7,700,295 B2 | 4/2010 | Baranov et al. |
| 7,728,287 B2 | 6/2010 | Felton et al. |
| 2002/0005479 A1 | 1/2002 | Yoshinari et al. |
| 2007/0164216 A1* | 7/2007 | Fedorov ............ B82Y 35/00 250/309 |
| 2007/0178607 A1 | 8/2007 | Prober et al. |
| 2008/0113875 A1 | 5/2008 | Chaurand et al. |
| 2008/0210857 A1 | 9/2008 | Felton et al. |
| 2010/0144056 A1 | 6/2010 | Winnik et al. |
| 2010/0255602 A1 | 10/2010 | Felton et al. |
| 2011/0195862 A1 | 8/2011 | Pett-Ridge et al. |
| 2011/0223613 A1 | 9/2011 | Gut |
| 2012/0077714 A1 | 3/2012 | Nolan et al. |
| 2013/0122516 A1 | 5/2013 | Hong et al. |

FOREIGN PATENT DOCUMENTS

| | | |
|---|---|---|
| WO | WO 2011/144914 A2 * | 11/2011 |
| WO | 2012003478 A2 | 10/2012 |
| WO | WO2014079802 | 5/2014 |
| WO | WO2014169394 | 10/2014 |
| WO | WO2015128490 | 9/2015 |

OTHER PUBLICATIONS

Geisen, et al. "Highly multiplexed imaging of tumor tissues with subcellular resolution by mass cytometry", Nat Methods. Apr. 2014;11(4):417-22.
Angelo; et al., "Multiplexed ion beam imaging of human breast tumors", Nat. Med (Apr. 2014), 20(4):436-42.
Guerguin-Kerl; et al., "Progress in analytical imaging of the cell by dynamic secondary ion mass spectrometry (SIMS microscopy).", Biochim Biophys Acta. (Aug. 2005), 1724(3):228-38.
Lanni; et al., "Mass spectrometry imaging and profiling of single cells", J Proteomics (Aug. 2012), 75(16):5036-51.
Balter, et al., "Secondary ionization mass spectrometry imaging of dilute stable strontium labeling in dentin and enamel", Bone, 2008, 42(1): 229-234.
Hindie, et al., "Mapping the cellular distribution of labelled molecules by SIMS microscopy", Biology of the Cell, 1992, 74:81-88.
Kraft, et al., "Quantitative analysis of supported membrane composition using the NanoSIMS", Applied Surface Science, 2006, 252(19): 6950-6956.
Lemaire, et al., "Tag-Mass: Specific Molecular Imaging of Transcriptome and Proteome by Mass Spectrometry Based on Photocleavable Tag", Journal of Proteome Research, 2007, 6(6): 2057-2067.
McMahon, et al., "Quantitative imaging of cells with multi-isotope imaging mass spectrometry (MIMS)—Nanoautography with stable isotope tracers", Applied Surface Science, 2006, 252(19): 6895-6906.

* cited by examiner

MULTIPLEXED IMAGING OF TISSUES USING MASS TAGS AND SECONDARY ION MASS SPECTROMETRY

CROSS-REFERENCING

This application claims the benefit of U.S. provisional patent application Ser. Nos. 61/877,733, filed on Sep. 13, 2013, and 61/970,803, filed on Mar. 26, 2014, which applications are incorporated by reference in their entireties.

GOVERNMENT RIGHTS

This invention was made with Government support under contract nos. CA034233, AI057229, CA130826, EY018228, HHSN272200700038C, 1K99 GM104148-01 awarded by the National Institutes of Health. The Government has certain rights in the invention.

BACKGROUND

Antibodies were first employed in tissue section analysis in 1942 to visualize pneumococcal antigens in organ biopsies from mice infused with live bacteria. Since that time, immunohistochemistry (IHC) has become a mainstay of clinical diagnostics and basic research that is primarily used to assess the spatial distribution of one or two (rarely more) antigens in tissue sections. Despite the high specificity of many antibodies, the concentration of most antigens is insufficient to permit detection by conventional assays without signal amplification. Signal amplification is typically achieved using multivalent, enzyme-linked secondary antibodies that bind the Fc portion of the primary antibody. In bright-field microscopy, the most commonly used enzymatic reporter is horseradish peroxidase, typically used to oxidize 3,3'-diaminobenzidine (DAB), resulting in accumulation of a brown precipitate. Still, the use of secondary antibodies combined with their poor correlation to the primary antigen concentration due to non-linear staining limits both reliable multiplexing and quantitation.

Simultaneous detection of multiple antigens can be subject to additional constraints that limit the utility of existing IHC-based analysis for predictive biomarker development in human clinical trials and clinical diagnostics. Colorimetric detection of four antigens has been reported using multiple enzyme-linked secondary antibodies, but in practice this approach is usually limited to two because of difficulties encountered in sample preparation and imaging. Fluorescent labels can provide a higher signal-to-noise ratio and are more frequently used for simultaneous detection of multiple molecular targets. Practical limitations include the need for primary antibodies generated in dissimilar host species and for non-overlapping reporter emission spectra. This conventional IHC methodology thus does not support the robust generation of multiplexed, quantitative data needed to understand the relationship between tissue microarchitecture and expression at a molecular level.

SUMMARY

A method of generating a high resolution two-dimensional image of a sample comprising cells and extracellular structures is provided. In certain embodiments, the method comprises: labeling a sample with at least one mass tag, thereby producing a labeled sample; scanning the sample with a secondary ion mass spectrometer (SIMS) ion beam to generate a data set that comprises spatially-addressable measurements of the abundance of said mass tag is across an area of the sample; and outputting the data set. In many embodiments, the data set contains the identity and abundance of the, mass tag.

The sample may be labeled with the at least one mass tag in a variety of different ways. For example, the mass tag comprised by a histochemical stain, or it may be conjugated to a capture agent, e.g., an antibody. In other cases, the sample may have been fed a mass tag while it was living, and the mass tag may have been incorporated into other molecules in the sample by metabolism.

In certain embodiments, the labeling step may involve contacting the sample with at least two different specific binding reagents, each comprising a different mass tag. In these embodiments, the sample may be scanned to generate a data set that comprises spatially-addressable measurements of the abundance of each of the mass tags across an area of the sample.

In particular embodiments, labeling may be done using a specific binding reagent, e.g., an antibody that contains a chelated atom that functions as the mass tag, methods for making which are known. In some embodiments, the mass tag may have a mass in the range of 12-238 atomic mass units, e.g., 21 to 238 atomic mass units, including C, O, N and F adducts. In some embodiments, the mass tag may be an atom of an element having an atomic number in the range of 21-90, e.g., an element having an atomic number of 21-29, 39-47, 57-79 or 89. In some cases, the element is a lanthanide.

In some cases, the method may comprise constructing an image of the sample from the data set. In some embodiments, the resolution of the image may be up to 1 nm, 5 nm, e.g., up to 10 nm, up to 50 nm, up to 100 nm, up to 500 nm, or up to 5000 nm.

In some embodiments, the method may further comprise defining the boundaries of individual cells (and, optionally, subcellular features in individual cells or other features of interest) in the image by segmenting the image, methods for which are known. In these embodiments, the method may further comprise integrating the data that corresponds to each the individual cells in the image, or a subcellular feature thereof, which may provide a set of values (each corresponding to an individual mass tag), that describe the cell as a whole. This embodiment of the method may further comprise categorizing the individual cells (e.g., into cell types or into normal or not normal, etc.) based on the integrated data obtained for each of is the cells. In these embodiments, the method may further comprise displaying an image of the tissue sample, in which the cells are color-coded by their category (i.e., where the cells of a first category are indicated in a first color, the cells of a second category are indicated in a second color and the cells of a third category are indicated in a third color, etc.). In some cases, in any one pixel of the image, the intensity of the color of the pixel may correlate with the integrated magnitude of the signals obtained for that pixel obtained by the scanning.

In some embodiments, the tissue sample is mounted on a conductive substrate, and the scanning is done by rastering the ion beam across the sample. The method may be performed on any suitable sample, including those from plants, animals, and sections that include microbial, e.g., bacterial, cells. In particular embodiments, the sample may be a tissue section, e.g., a formalin-fixed, paraffin-embedded (FFPE) section, that has a thickness in the range of, e.g., 2 to 20 microns (e.g., 3 to 12 microns).

Also provided is a system for analyzing a sample. This system may comprise: a) a secondary ion mass spectrometry (SIMS) system that comprises a holder for retaining a substrate comprising a sample, wherein the system is configured to (i) scan the sample with a SIMS ion beam and generate a data set that comprises measurements of the abundance of a specific binding reagent that is bound to the sample and (ii) output the data set; and b) a computer comprising an image analysis module that processes the data set to produce an image of the sample. The holder is in a movable stage that can be controllably moved (e.g., stepped or continuously moved) in at least in the x and y directions (which are in the plane of the sample) to facilitate scanning. The image analysis module can be programmed to perform many of the steps of the method described above. For example, in some embodiments, the image analysis module may segment the image to identify the boundaries of individual cells, and, optionally, subcellular features in individual cells, in the image. In some cases, the image analysis module may integrate the data for each of the individual cells or a subcellular feature thereof in the image and optionally categorize the individual cells based on the integrated data obtained for each of the cells. The image analysis module may also displays an image of the tissue sample, wherein the cells are color-coded by their category. As noted above, in any one pixel of the image, the intensity of the color of the pixel correlates with the magnitude of the signals obtained for that pixel obtained by the SIMS system.

BRIEF DESCRIPTION OF THE FIGURES

The patent or application file contains at least one drawing executed in color. Copies of this patent or patent application publication with color drawing(s) will be provided by the Office upon request and payment of the necessary fee.

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
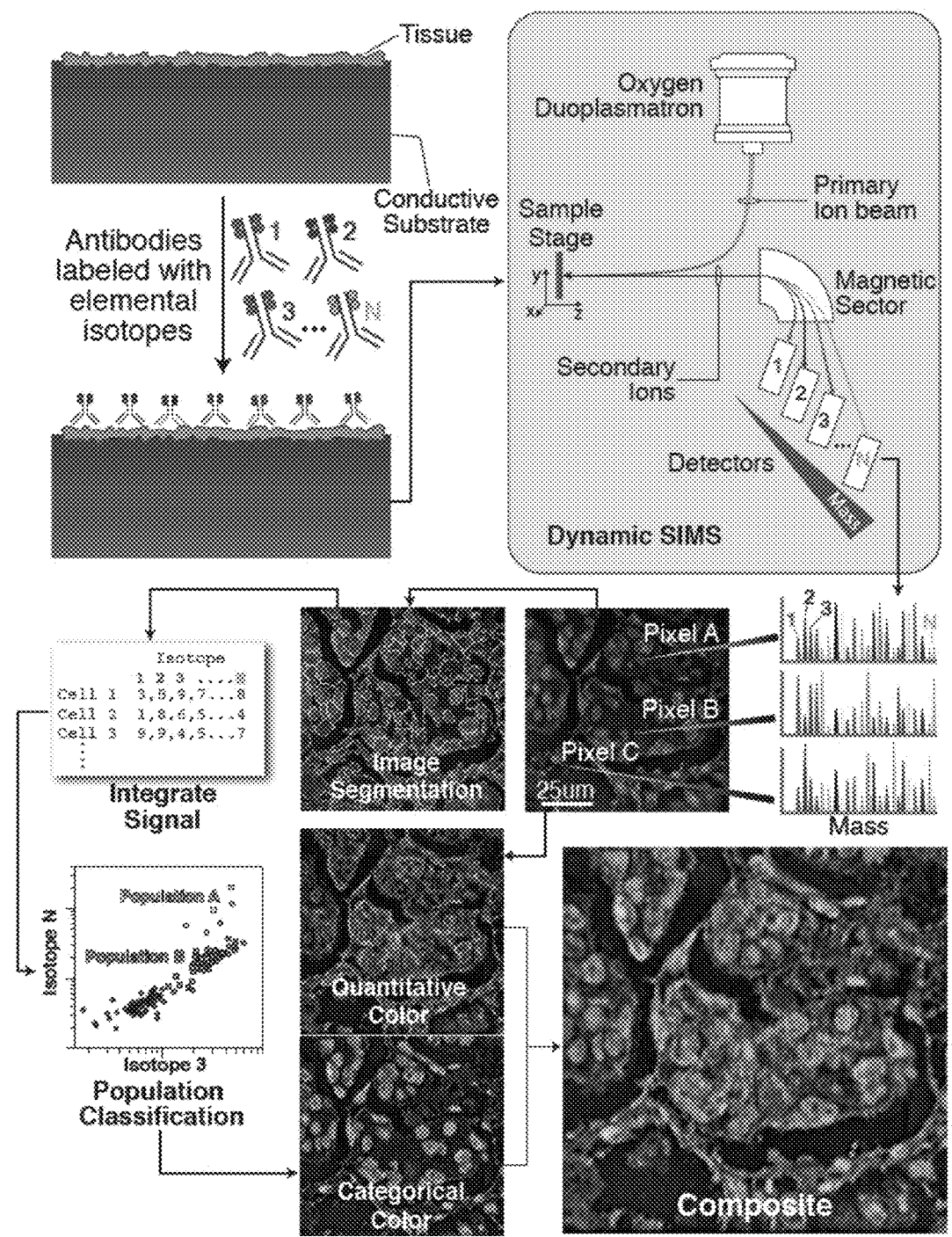
FIG. 1. Workflow summary of multiplexed ion beam imaging (MIBI). Biological specimens, such as FFPE tissue or cell suspensions, are immobilized on a conductive substrate, such as indium tin oxide coated glass or silicon wafer. Samples are subsequently stained with antibodies conjugated to unique transition element isotope reporters, dried, and loaded under vacuum for MIBI analysis. The sample surface is rasterized with a primary ion beam (O-) that sputters the antibody-specific isotope reporters native to the sample surface as secondary ions. An elemental mass spectrum is acquired for each pixel. Regions of interest demarcating nuclear and cytosolic compartments of each cell are integrated, tabulated, and categorized. Composite images comprised of pseudo-colored categorical features and quantitative three-color overlays are constructed to summarize multidimensional expression data.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "labeling" refers to attaching a detectable moiety to an analyte such that the presence and/or abundance of the analyte can be determined by evaluating the presence and/or abundance of the label. The term "labeling" includes labeling using a histological stain (in which case the mass tag may be part of or conjugated to the stain) as well as labeling using a capture agent, e.g., an antibody or an oligonucleotide probe, that has been conjugated to a mass tag. A sample can also be labeled by feeding the sample with a mass-tagged compound (e.g., IdU or BrdU) that is metabolized and incorporated into the sample prior to fixation.

As used herein, the term "biological feature of interest" refers to any part of a cell that can be stained or indicated by binding to an antibody. For example, stains may be used to define and examine bulk tissues (highlighting, for example, muscle fibers or connective tissue), cell populations (classifying different blood cells, for instance), or organelles within is individual cells. Stains may be class-specific (DNA, proteins, lipids, carbohydrates). Exemplary biological features of interest include cell walls, nuclei, cytoplasm, membrane, keratin, muscle fibers, collagen, bone, proteins, nucleic acid, fat, etc. A biological feature of interest can also be indicated by immunohistological methods, e.g., using a capture agent such as an antibody that is conjugated to a label. In these embodiments, the capture agent binds to an epitope, e.g., a protein epitope, in the sample. Exemplary epitopes include, but are not limited to carcinoembryonic antigen (for identification of adenocarcinomas, cytokeratins (for identification of carcinomas but may also be expressed in some sarcomas) CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

As used herein, the term "multiplexing" refers to using more than one label for the simultaneous or sequential detection and measurement of biologically active material.

As used herein, the term "specific binding reagent" refers to a labeled reagent that can specifically bind to one or more sites in a specific molecular target (e.g., a specific protein, phospholipid, DNA molecule, or RNA molecule) in or on a cell. Specific binding reagents include antibodies, nucleic acids, and aptamers, for example. A used herein, an "aptamer" is a synthetic oligonucleotide or peptide molecule that specifically binds to a specific target molecule.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light is chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding reagent and analyte when they are specifically bound in a capture agent/analyte complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M or less.

As used herein, the term "mass tagged" refers to a molecule that is tagged with either a is single kind of stable isotope that is identifiable by its unique mass or mass profile or a combination of the same, where the combination of stable isotopes provides an identifier. Combinations of stable isotopes permit channel compression and/or barcoding. Examples of elements that are identifiable by their mass include noble metals and lanthanide, although other elements may be employed. An element may exist as one or more isotopes, and this term also includes isotopes of positively and negatively metals. The terms "mass tagged" and "elementally tagged" may be used interchangeably herein.

As used herein, the term "mass tag" means any isotope of any element, including transition metals, post transition metals, halides, noble metal or lanthanide, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type).

As used herein, the term "lanthanide" means any element having atomic numbers 58 to 71. Lanthanides are also called "rare earth metals".

As used herein, the term "noble metal" means any of several metallic elements, the electrochemical potential of which is much more positive than the potential of the standard hydrogen electrode, therefore, an element that resists oxidation. Examples include palladium, silver, iridium, platinum and gold.

As used herein, the term "elemental analysis" refers to a method by which the presence and/or abundance of elements of a sample are evaluated.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

A "sample comprising cells" is a sample of biological origin that contains intact, e.g., fixed, cells. In some embodiments, the sample may be substantially planar. Examples of such samples include tissue sections, samples that are made by depositing disassociated cells onto a planar surface, and samples that are made by growing a sheet of cells on a planar surface.

As used herein, the term "scanning" refers to a method by which a source of radiation is (e.g., a laser) is zig-zagged or rastered over a surface until a substantial two dimensional area has been irradiated by the source of energy.

As used herein, the term "spatially-addressable measurements" refers to a set of values that are each associated with a specific position on a surface. Spatially-addressable measurements can be mapped to a position in a sample and can be used to reconstruct an image of the sample.

As used herein, the term "across an area", in the context of spatially-addressable measurements of the abundance of a mass tag across an area of a sample, refers to measurements of mass tags that are at or under (e.g., on or within cells that are proximal to) the surface of the sample. The depth of the area analyzed can vary depending on the energy of the ion beam.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

The method described herein employs a mass tag, i.e., a stable isotope that is identifiable by its mass for labeling of a biological sample that contains cells and extracellular structures, measured on an instrument capable of quantifying elemental composition with spatial registration using a secondary ion mass spectrometer (SIMS), e.g., static or dynamic SIMS.

The mass tag may be part of or conjugated to a stain, or conjugated to a capture agent such as an antibody. In certain embodiments, mass tags may be composed of a chelating polymer made up of repeating units of a metal chelator, such as ethylenediaminetetraacetic acid (EDTA) or diethylene triamine pentaacetic acid (DTPA), chelated to one or more atoms of a single non-biological isotope. In some embodiments the mass tags may be substantially is uniform in size, so the abundance of specific binding reagent will be in direct proportion with the number of tag atoms. The tagged specific binding reagent is then contacted with a biological sample, washed, and measured with an SIMS instrument capable of quantifying the number of tag atoms present in the sample with spatial registration. The abundance of the analyte may be inferred from the molar ratio of tag atoms per detection reagent.

The method described above may be multiplexed in that the assay can be done using multiple specific binding reagents (e.g., more than 2 specific binding reagents, up to 5 specific binding reagents, up to 10 specific binding reagents, up to 20 specific binding reagents, up to 50 specific binding reagents or up to 100 specific binding reagents or more). Each specific binding reagent may be linked to a different mass tag, where the mass tags are distinguishable from one another by secondary ion mass spectrometry. Alternatively or in addition, multiplexing may involve using stains for specific features of interest.

Many elements exist in nature as multiple stable isotopes. For example, $^{153}$Eu accounts for 52% of europium on Earth and $^{151}$Eu makes up most of the remaining 48%, while unstable, radioactive isotopes of europium constitute less than 1%. Many stable isotopes are commercially available as powders or salt preparations, in varying degrees of purity, including 99% (2N), 99.9% (3N), 99.99% (4N), 99.999% (5N) and 99.9999% (6N) pure. In some embodiments, metal chelator tags may be synthesized using enriched isotopes. For example, mass dots may be synthesized using 151Eu (e.g. Europium 151 Oxide, 99.999% purity, American Elements). Mass dots are described in US patent publication 2012/0178183 A1, which is incorporated herein by reference. Using enriched isotopes maximizes the number of unique species of isotope tags that can be simultaneously detected in a multiplexed analysis. In addition, spatially distinct features of interest may be labeled with the same metal tag to further multiplex the analysis. Such spatially distinct features may be distinguished based on co-localization with one or more other metal tags. For example, a Her2 membrane stain and an ER nuclear stain using the same metal tag may be distinguished from one based on a dsDNA or histone H3 stain that uses a different metal tag, which would co-localize with the ER stain.

The mass tag may be part of or conjugated to a stain. In these embodiments, the stain may be phalloidin, gadodiamide, acridine orange, bismarck brown, barmine, Coomassie blue, is bresyl violet, brystal violet, DAPI, hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nulear envelope, and so forth), a compartment of the cell (e.g., cytosol, nuclear fraction, and so forth). The stain may enhance contrast or imaging of intracellular or extracellular structures.

In certain embodiments, the stain may be suitable for administration to a live subject. The stain may be administered to the subject by any suitable means, such as ingestion, injection (e.g., into the blood circulation), or topical administration (e.g., during a surgery). Such a stain may be specific for a tissue, biological structure (e.g., blood vessel, lesion), or cell type of interest. The stain may be incorporated into cells of the subject of a cellular process, such as glucose uptake. Examples of such stains include, without limitation, gadolinium, cisplatin, halogenated carbohydrates (e.g., carbohydrates which are fluorinated, chlorinated, brominated, iodinated), and so forth. Other injectable stains used in imaging techniques (e.g., such as MRI, PET scans, CT scans and so forth) may be conjugated to a mass tag if not inherently associated with a mass tag, and administered to a live subject. A sample may be obtained from the subject after administration, for use in the methods described herein.

In other embodiments, and as will be described in greater detail below, the mass tag may be conjugated to a capture agent, e.g., an antibody that recognizes an epitope on the sample. In a multiplexed assay, a combination of capture agents and stains may be used.

The mass tag used in the method may be any stable isotope that is not commonly found in the sample under analysis. These may include, but are not limited to, the high molecular is weight members of the transition metals (e.g. Rh, Ir, Cd, Au), post-transition metals (e.g. Al, Ga, In, Tl), metalloids (e.g. Te, Bi), alkaline metals, halogens, and actinides, although others may be used in some circumstances. A mass tag may have a mass in the range of 21 to 238 atomic mass units. In certain embodiments, a lanthanide may be use. The lanthanide series of the periodic table comprises 15 elements, 14 of which have stable isotopes (La, Ce, Pr, Nd, Sm, Eu, Gd, Tb, Dy, Ho, Er, Tm, Yb, Lu). Lanthanindes can be readily used because of their rarity in the biosphere. There are greater than 100, non-biological stable isotopes of elements between 1 and 238 AMU. In some embodiments, tagging isotopes may comprise non-lanthanide elements that can form stable metal chelator tags for the applications described herein. In SIMS-based measurement modality, unlike some ICP-MS-based modalities, the elemental reporter could also consist of lower MW, transition elements not common in biological matrices (e.g. Al, W, and Hg).

Elements suitable for use in this method in certain embodiments include, but are not limited to, lanthanides and noble metals. In certain cases, an elemental tag may have an atomic number of 21-90. In particular embodiments, the elemental tag may contain a transition metal, i.e., an element having the following atomic numbers, 21-29, 39-47, 57-79, and 89. Transition elements include the lanthanides and noble metals. See, e.g., Cotton and Wilkinson, 1972, pages 528-530. The elemental tags employed herein are non-biological in that they are man made and not present in typical biological samples, e.g., cells, unless they are provided exogenously.

In particular embodiments, the mass tag to be linked to the binding reagent may be of the formula: R-MT, where R is a reactive group that can form a linkage with a reactive group on a specific binding reagent and MT is a mass tag. The compound may also contain a spacer between R and MT. In particular embodiments, R may be, e.g., a maleimide or halogen-containing group that is sulhydryl reactive, an N-hydroxysuccinimide (NHS)-carbonate that is amine-reactive or an N,N-diisopropyl-2-cyanoethyl phosphoramidite that is hydroxyl-reactive. Such groups react with other groups on the specific binding reagent, e.g., a cysteine or other residue of an antibody or a sulfhydryl group of an oligonucleotide). In many embodiments, the linkage between the reactive group and the mass tag is not selectively cleavable, e.g., is not is photo-cleavable.

In particular embodiments, MT may be a polymer of, e.g., 10-500 units, where each unit of the polymer contains a coordinated transition metal. Suitable reactive groups and polymers containing coordinating groups, including DOTA and DTPA-based polychetants, are described in a variety of publications, including: Manabe et al. (Biochemica et Biophysica Acta 883: 460-467 (1986)) who describes attaching up to 105 DTPA residues onto a poly-L-lysine backbone using the cyclic anhydride method and also attaching polylysine-poly-DTPA polychelants onto monoclonal antibody (anti-HLA IgG$_1$) using a 2-pyridyl disulphide linker achieving a substitution of up to about 42.5 chelants (DTPA residues) per site-specific macromolecule; Torchilin (U.S. Pat. No. 6,203,775) who describes a generic method for labeling antibodies that includes an antibody-reactive, lanthanide chelating compound of a generic formula; Sieving (U.S. Pat. No. 5,364,614), the abstract for describes a DOTA-based polychetant containing a polylysine backbone that is linked to a protein. Further descriptions of such moieties are described in, for example: US20080003616 (Polymer backbone element tags), U.S. Pat. No. 6,203,775 (Chelating polymers for labeling of proteins), U.S. Pat. No. 7,267,994 (Element-coded affinity tags), U.S. Pat. No. 6,274,713 (Polychelants) and U.S. Pat. No. 5,364,613 (Polychelants containing macrocyclic chelant moieties), as well as many others. These publications are incorporated by references for their generic and specific teachings of reactive groups and polymers containing coordinating groups, as well as the methods that can make such compounds. In addition to the methods described in the references cited above, methods for making polymer-based elemental tags are also described in detail in Zhang et al (Agnew Chem. Int. Ed. Engl. 2007 46: 6111-6114). In addition, any chelator able to bind to metal tags can be used. These include EDTA, EGTA, and Heme. These chelators are able to bind to +1, +2, +3, +4 ions of metal tags. Methods for linking such tags to binding reagents are known in the art. For example, the MAXPAR reagents produced by DVS Sciences is a maleimide-functionalized polymer of DTPA, with an average length of 30 monomers. Using the MAXPAR protocol, it is possible to conjugate a typical IgG antibody with 6 or 7 polymers, thereby conjugating an average of 200 tagging isotope atoms per antibody.

When using mass-based elemental analysis there are more than 100 non-biological elemental isotopic masses available between 21 and 238 atomic mass units (amu) that can be is simultaneously measured with virtually no overlap. Because these rare earth metals are not usually present in biological isolates, the only limitations of detection are the sensitivity of the reagents to which they are conjugated, and the sensitivity of the instrument performing the measurement.

In particular embodiments, the method described above may be employed in a multiplex assay in which a heterogeneous population of cells is labeled with a plurality of distinguishably mass tagged binding reagents (e.g., a number of different antibodies). As there are more than 80 naturally occurring elements having more than 200 stable isotopes, the population of cells may be labeled using at least 5, at least 10, at least 20, at least 30, at least 50, or at least 100, up to 150 or more different binding reagents (that bind to, for example different cell surface markers) that are each tagged with a different mass. After the population of cells is labeled, they are analyzed using the method described above.

As noted above, the specific binding reagent used in the method may be any type of molecule (e.g., an antibody, a peptide-MHC tetramer, a nucleic acid (e.g., ssRNA or ssDNA), an aptamer, a ligand specific for a cell surface receptor, etc.) that is capable of specific binding to a binding partner in or on cells. The binding partner may be a protein, a nucleic acid or another type of cellular macromolecule (e.g., a carbohydrate). The binding partner may be on the cell surface, or it may be extracellular or intracellular (e.g., associated with the nucleus or another organelle, or cytoplasmic).

In certain aspects, a specific binding reagent may be an MT conjugated to a nucleic acid that hybridizes to a specific RNA and/or DNA sequence. The MT conjugated nucleic acid may be used in combination with any suitable technique for detecting a target (e.g., RNA, DNA, protein or protein complex), such as standard in-situ hybridization, In-situ hybridization utilizing branched DNA probes (e.g., as provided by Affymetrix), proximity ligation (PLA) and rolling circle amplification (e.g., as provided by Olink bioscience), and so forth. In-situ hybridization techniques, including those employing branched DNA probes are described by Monya Baker et al. (Nature Methods 9, 787-790 (2012)). Briefly, in-situ hybridization using branched DNA probes utilizes a series of ssDNA probes, where a first set of DNA probes specifically hybridizes to the target DNA or RNA sequence, and a second set of DNA probes may hybridize to a portion of the first set of DNA probes, thus expanding the number of DNA is probes that can bind (indirectly) to a single DNA or RNA molecule. A third set may bind to the second set of DNA probes in a likewise manner, and so forth. One or more of the sets of DNA probes may be conjugated to a metal tag to label the target DNA or RNA molecule. Proximity ligation techniques, including detection of single RNA molecules, DNA molecules, and protein complexes are described by Weibrecht et al. (Nature Methods 9, 787-790 (2012)) which is incorporated herein by reference. Rolling circle amplification is described by Larsson et al. (Nat. Methods 1, 227-232 (2004)), which is incorporated herein by reference. Briefly, in proximity ligation followed by rolling circle amplification, a nucleic acid is hybridized to two proximal RNA or DNA strands, after which the nucleic acid is ligated and then amplified, resulting in many copies of the sequence complimentary to the nucleic acid. The complimentary sequence is therefore present in higher copy number than the original proximal RNA or DNA strands, and can be more easily detected (e.g., by a MT conjugated nucleic acid that hybridizes to the complimentary sequence). The proximal RNA or DNA stands may each be conjugated to a different antibody (e.g., where the different antibodies may each be specific for a different protein of a protein complex).

Any of the above techniques may be used to resolve single molecular targets (e.g., individual RNA molecules, DNA molecules, proteins or protein complexes). As single molecular targets may be resolvable as discrete puncti, a combination of metal isotopes may be used to uniquely label the molecular target. In one example, the specific binding reagent may be a nucleic acid may be conjugated to a unique combination of metal isotopes. In another example, a combination of MT conjugated nucleic acids (e.g., each conjugated to a different mass tag) may be used together to label the molecular target with a unique combination of metal isotopes. As such, n number of mass tags could be combinatorially used to label $2^n$ different molecular targets, provided that the molecular targets can be spatially distinguished. The method described herein may be used to assay a sample of biological origin that contains cells, in which the amounts of certain components (e.g., protein, nucleic acid or other molecules) need to be determined. In some embodiments, this analysis may be done using a SIMS instrument (e.g. NanoSIMS by Cameca, NanoTOF by Physical Electronics). Secondary Ion Mass Spectrometry is a surface sensitive technique that allows the detection and is localization of the chemical composition of sample surfaces. The instrument may use a finely focused, pulsed primary ion beam to desorb and ionize molecular species from a sample surface. The resulting secondary ions are transferred into a mass spectrometer, where they are mass analyzed and quantified using standard mass analyzers (e.g., time-of-flight, magnetic sector, quadrupole, ion trap, or a combinations thereof). Displaying the mass spectra that were collected from the sample surface generates chemical images. Each pixel in the resulting essentially represents a mass spectrum. Notably, this instrument would only require 'unit resolution'—the ability to discriminate mass reporters separated by 1 AMU or more. NanoTOF uses a low intensity, pulsed source that is synced with the TOF detector. Cameca uses a DC beam (i.e. continuous and not pulsed).

When high-speed pulsed or continuous ion beams (primary ions) are irradiated onto the surface of a solid sample at a high vacuum, a component of the surface is released into the vacuum by a desorption-ionization phenomenon. The generated positively or negatively-charged ions (secondary ions) are focused in one direction by an electrical field, and detection is performed at a remote position. When pulsed primary ions are irradiated onto the solid surface, secondary ions having various masses are generated depending on the composition of the surface of the sample. Among the secondary ions, an ion having a smaller mass flies faster than an ion having a larger mass in a TOF tube. Therefore, a measurement of a time between generation and detection of the secondary ions (flight time) enables the analysis of masses of the generated secondary ions to be performed. When primary ions are irradiated, only secondary ions generated at the outermost surface of a solid sample are released into the vacuum, so that information about the outermost surface (e.g., a depth of less than 1 nm, less than 2 nm, less than 5 nm, less than 10 nm, less than 20 nm, less than 50 nm, less than 100 nm, or more than 100 nm) of the sample can be obtained. In the TOF-SIMS, the amount of irradiated primary ions is significantly small, so that an organic compound is ionized while maintaining its chemical structure, and the structure of the organic compound can be identified from the mass spectra. The principles of secondary ion mass spectrometry are described in, e.g., Belu et al (Biomaterials. 2003 24: 3635-53), P61 et al (Histochem Cell Biol. 2010 134: 423-43) and Klitzing (Methods Mol Biol. 2013 950: 483-501).

As noted above, after the initial data is obtained, the data is used to construct an image is of the sample. This image may be analyzed to identify the boundaries of individual cells, and/or subcellular features in individual cells, in the image. Computer-implemented methods for segmenting images of cells are known in the art and range from relatively simple thresholding techniques (see, e.g., Korde, et al Anal Quant Cytol Histol. 2009 31, 83-89 and Tuominen et al Breast Cancer Res 2010 12, R56), to more sophisticated methods, such as, for instance, adaptive attention windows defined by the maximum cell size (Ko et al. J Digit Imaging 2009 22, 259-274) or gradient flow tracking (Li, et al. J Microsc 2008 231, 47-58). Some suitable image segmentation methods may be reviewed in Ko et al (J Digit Imaging. 2009 22: 259-74) and Ong (Comput Biol Med. 1996 26:269-79). Next the data that corresponds to each of the individual cells, or a subcellular feature thereof, that have been defined by the segmenting are integrated to provide, for each cell, values that represent the amount of each of the mass tags within the boundary of each cell. This step of the method results in a data set that contains, for each cell, measurements of the amount of each of the mass tags that are associated with the cell. This concept is illustrated in the table shown below.

|        | Tag 1 | Tag 2 | Tag 3 | Tag 4 | Tag 5 |
|--------|-------|-------|-------|-------|-------|
| Cell 1 | 0.1   | 0.1   | 5     | 3     | 1     |
| Cell 2 | 0.2   | 0.4   | 4     | 0.1   | 0.1   |
| Cell 3 | 10    | 0.1   | 0.2   | 0.3   | 5     |

This data allows one to categorizing the cells in the sample. For example, in the example shown in the table above, the three cells are likely to be different types of cells because they have different profiles of mass tags where the profile identifies the category. In particular cases, this information may be used to provide a false-color image in which each of the cells is color-coded by their category. As such, this method may comprise displaying an image of the sample, in which the cells are color-coded by their category. In particular embodiments, in any one pixel of the image, the intensity of the color of the pixel correlates with the magnitude of the signals obtained for that pixel obtained in the original scanning. In these embodiments, the resulting false color image may show color-code cells in which the intensity of the color in any single pixel of a cell correlates with the amount of specific binding reagent that is associated with the corresponding area in the sample.

As the original scan may only result in partial removal of the sample (e.g., at a depth is on the nanometer scale), the sample may be re-scanned to generate an additional data set having measurements of the abundance of one or more mass tags across the area that was originally scanned. For example, the original scan may be used to identify an area or areas of interest in the sample. Such a scan may be lower resolution and may therefore be more rapid, measure the mass tag abundance in a larger area at a time, and/or may result in removal of less of the sample. The re-scan may be a higher resolution scan of the abundance of metal tags in the area or areas of interest. Alternatively or in addition, multiple scans across the same area may be used to produce a 3 dimensional image (e.g., compiled from the individual 2 dimensional data sets). In certain aspects, areas of interest identified by an original scan may be analyzed further after isolation of the area of interest from the sample, e.g., such as by laser capture micro dissection.

The methods described herein may include normalization as a means of standardizing data obtains across samples and/or time-points (e.g., to enable quantitative cross-sample comparison). In certain aspects, normalization of ionization and/or overall measurement efficiency may be performed using standardized metal particles or suspension present in the sample. The standardized metal particles or suspension may have a known amount of one or more mass tags, and the resulting measurement of the one or more mass tags may be used to normalize the measurements of other mass tags in the sample. For example, normalization beads may be used to calibrate the system or normalize data obtained by the subject methods. Normalization of mass cytometry data using bead standards is described by Rachel Fink et al. (Cytometry A. 83(5):483-94(2013)), which is incorporated herein by reference, and is applicable to the subject methods which also utilize time of flight mass spectrometry. Alternatively or in addition, ionization and/or measurement efficiency may be normalized according to any of the above-mentioned stains. For example, measurements of a mass tag used to stain the ER may be normalized to the overall intensity of that mass tag in a given area, in the cell, or across multiple cells in the sample.

Normalization may also be used to account for the effects of, for example, degree of tissue fixation, retention of protein, and staining efficiency with specific binding reagents. Mass tags conjugated to well-characterized antibodies that bind molecular targets stably expressed across a wide range of cell types may be used for normalization. Such antibodies is include, without limitation, antibodies to housekeeping proteins (such as GAPDH, HSP90, beta-actin and beta-tubulin), dsDNA and histone H3.

As discussed above, the methods of the subject invention allow for a multiplexed approach. Multiple mass tags may be measured to determine the abundance of multiple molecular targets (e.g. specific proteins, DNA, RNA, etc.) as well as biologic features of interest in the sample (e.g., cell or tissue structure, cellular organelles, cellular fractions, etc.). In addition, mass tag measurements may be normalized according to any of the above-described embodiments. The large number of discrete mass tags enables multiplexing of more than 2, 5, 10, 20, 30, 40, 50, 60, 70, 80, 100 or more different mass tags in a single area. Multiple mass tags (e.g., conjugated to antibodies against complementary epitopes of the same molecular target) may be used for redundancy so as to increase confidence in a measurement of a specific molecular target. Further multiplexing may be achieved by using identical mass tags to label two or more spatially distinct targets or features of interest. Alternatively or in addition, a unique combination of metal tags may be used to identify a spatially distinct target or feature of interest.

Systems

Also provided is a system for analyzing a sample. This system may comprise: a) a secondary ion mass spectrometry (SIMS) system that comprises a holder for retaining a substrate comprising a sample, wherein the system is configured to (i) scan the sample with a primary ion beam (e.g., a beam of oxygen, cesium, gold, argon, bismuth, xenon, C60, $SF_6$, or gallium ions, or any mixture there, e.g., a mixture of oxygen and xenon ions) and generate a data set that comprises mass-specific abundance measurements of a specific binding reagent that is bound to the sample and (ii) output the data set; and b) a computer comprising an image analysis module that processes the data set to produce an image of the sample. The holder is in a movable stage that can be controllably moved (e.g., stepped or continuously moved) in at least the x and y directions (which are in the plane of the sample) to facilitate scanning. The image analysis module can be programmed to perform many of the steps of the method described above. For example, in some embodiments, the image analysis module may segment the image to identify the boundaries of individual cells, and, optionally, subcellular is features in individual cells, in the image. In some cases, the image analysis module may integrate the data for each of the individual cells or a subcellular feature thereof in the image and optionally categorize the individual cells based on the integrated data obtained for each of the cells. The image analysis module may also display an image of the tissue sample, wherein the cells and/or subcellular features thereof are color-coded by their category. As noted above, in any one pixel of the image, the intensity of the color of the pixel correlates with the magnitude of the signals obtained for that pixel obtained by the SIMS system. In a particular embodiment, the system may comprise a DC ion source (i.e. dynamic source) linked to a quadrapole, then to an ion pulser, then to a time of flight (TOF) tube. The SIMS system may be dynamic or static. NanoSIMS is considered a dynamic because it uses a higher power DC primary ion source, NanoTOF is considered static because it uses a lower power pulsed source.

The image analysis module may combine data sets obtained from multiple scanned areas into a single data set, wherein each of the multiple scanned areas are offset from one another. The image analysis module may adjust the offset between adjacent scanned areas so as to increase the overlap of pixels with similar mass tag intensities near the edges of the adjacent scanned areas.

The image analysis module may transform the data set into one or more false color images (e.g. pseudocolor, pseudobrightfield, pseudo-immunofluorescence). The image may be in any suitable image file format (e.g., JPEG, Exif, TIFF, GIF, PNG, a format readable by an image analysis software such as ImageJ, and so forth). In certain embodiments, the image analysis module may produce the image by transforming the abundance (e.g., measured intensity) of one or mass tags into the intensity of one or more false colors at individual pixels in the image. The relationship between the intensity of a mass tag and the intensity of the corresponding false color may be linear or non-linear (e.g., logarithmic, exponential, etc.).

In certain embodiments, the system is configured to generate a multiplexed data set comprising spatially-addressable measurements of the abundances of a plurality of mass tags that are bound to an area of the sample. The image analysis module may transform the plurality of mass tag measurements to produce a plurality of false color images. The image is analysis module may overlay the plurality of false color images (e.g., superimpose the false colors at each pixel) to obtain a multiplexed false color image. Multiple mass tag measurements (e.g., unweighted or weighted) may be transformed into a single false color, e.g., so as to represent a biological feature of interest characterized by the binding of the specific binding reagent associated with each of the multiple mass tags. False colors may be assigned to mass tags or combinations of mass tags, based on manual input from the user. Alternatively or in addition, an unsupervised approach may be used to determine groups of mass tags to be represented by a single false color. The unsupervised approach may identify groups of mass tags that maximizing variance while minimizing the number of groups (e.g., such as through principle component analysis (PCA)), grouping mass tags that are co-localized and/or in proximity (e.g., by any suitable clustering algorithm), or may employ any other suitable method for grouping mass tags to be represented by a single false color. In certain aspects, the image may comprise false colors relating only to the intensities of mass tags associated with a feature of interest, such as mass tags in the nuclear compartment (e.g., co-localized with a dsDNA specific mass tag).

The image analysis module may further be configured to adjust (e.g., normalize) the intensity and/or contrast of mass tag intensities or false colors, to perform a convolution operation (such as blurring or sharpening of the mass tag intensities or false colors), or perform any other suitable operations to enhance the image. In certain aspects, the image analysis module may compile data sets generated from multiple 2D scans to produce an image that is a 3D model of the cells. The image analysis module may perform any of the above operations to align pixels obtained from successive 2D scans and/or to blur or smooth mass tag intensities or false colors across pixels obtained from successive 2D scans to produce the 3D model.

The image analysis method may be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory is (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer, which runs the program, and returns an output to the user.

A system can in certain embodiments comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; d) system memory can also include read-only memory (ROM); a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can is have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of computer is controlled primarily by operating system, which is executed by central processing unit. The operating system can be stored in a system memory. In some embodiments, the operating system can includes a file system. In addition to an operating system, one possible implementation of the system memory includes a variety of programming files and data files for implementing the method described below. In certain cases, the programming can contain a program, where the program can be composed of various modules, and a user interface module that permits a user at user interface to manually select or change the inputs to or the parameters used by programming. The data files can include various inputs for the programming.

In certain embodiments, instructions in accordance with the method described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, is NJ), as well as any many others.

biological sample may be isolated from an individual, e.g., from a soft tissue or from a bodily fluid, or from a cell culture that is grown in vitro. A biological sample may be made from a soft tissue such as brain, adrenal gland, skin, lung, spleen, kidney, liver, spleen, lymph node, bone marrow, bladder stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc. Biological samples also include cells grown in culture in vitro. A cell may be a cell of a tissue biopsy, scrape or lavage or cells. In particular embodiments, the cell may of a cell in a formalin fixed paraffin embedded (FFPE) sample. In particular cases, the method may be used to distinguish different types of cancer cells in FFPE samples.

The method described above finds particular utility in examining tissue sections using panels of antibodies, examples of which are provided in the table below.

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel-Female) | CK7, CK20, mammaglobin, ER, TTF1, CEA, CA19-9, S100 synaptophysin, and WT-1. |
| Carcinoma Unknown Primary Site, Male (CUPS IHC Panel-Male) | CK7, CK20, TTF1, PSA, CEA, CA19-9, S100, and synaptophysin. |
| GIST IHC Panel | CD117, DOG-1 CD34 and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma INC Panel | CDX2, CK 20, CEA (monoclonal) CA19-9, PLAP CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHCPanel | Pan-CK, S100 CD45, and vimentin. |

Utility

The above-described method can be used to analyze a cells from a subject to determine, for example, whether the cell is normal or not or to determine whether the cells are responding to a treatment. In one embodiment, the method may be employed to determine the degree of dysplasia in cancer cells. In these embodiments, the cells may be from a sample of from a multicellular organism or a microbe. A In some embodiments, the method may involve obtaining an image as described above (an electronic form of which may have been forwarded from a remote location) and may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in is different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment, the sample pair is represented by undifferentiated cells, e.g., stem cells, and differentiated cells.

Cells any organism, e.g., from bacteria, yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

In order to further illustrate the present invention, the following specific examples are given with the understanding that they are being offered to illustrate the present invention and should not be construed in any way as limiting its scope.

Examples

Described below is an example of a method that uses secondary ion mass spectrometry to image antibodies via isotopically pure elemental metal reporters. Multiplexed ion beam imaging (MIBI) is capable of analyzing up to 100 or more targets simultaneously with 50-nm lateral resolution over a five log dynamic range. Here, MIBI is used to analyze formalin-fixed, paraffin-embedded (FFPE) human breast tumor tissue sections using 10 labels simultaneously. The resultant data suggest MIBI will provide new insights relating tissue microarchitecture and highly multiplexed protein expression patterns relevant to clinical diagnostics, basic research, and drug discovery.

Figure 3:
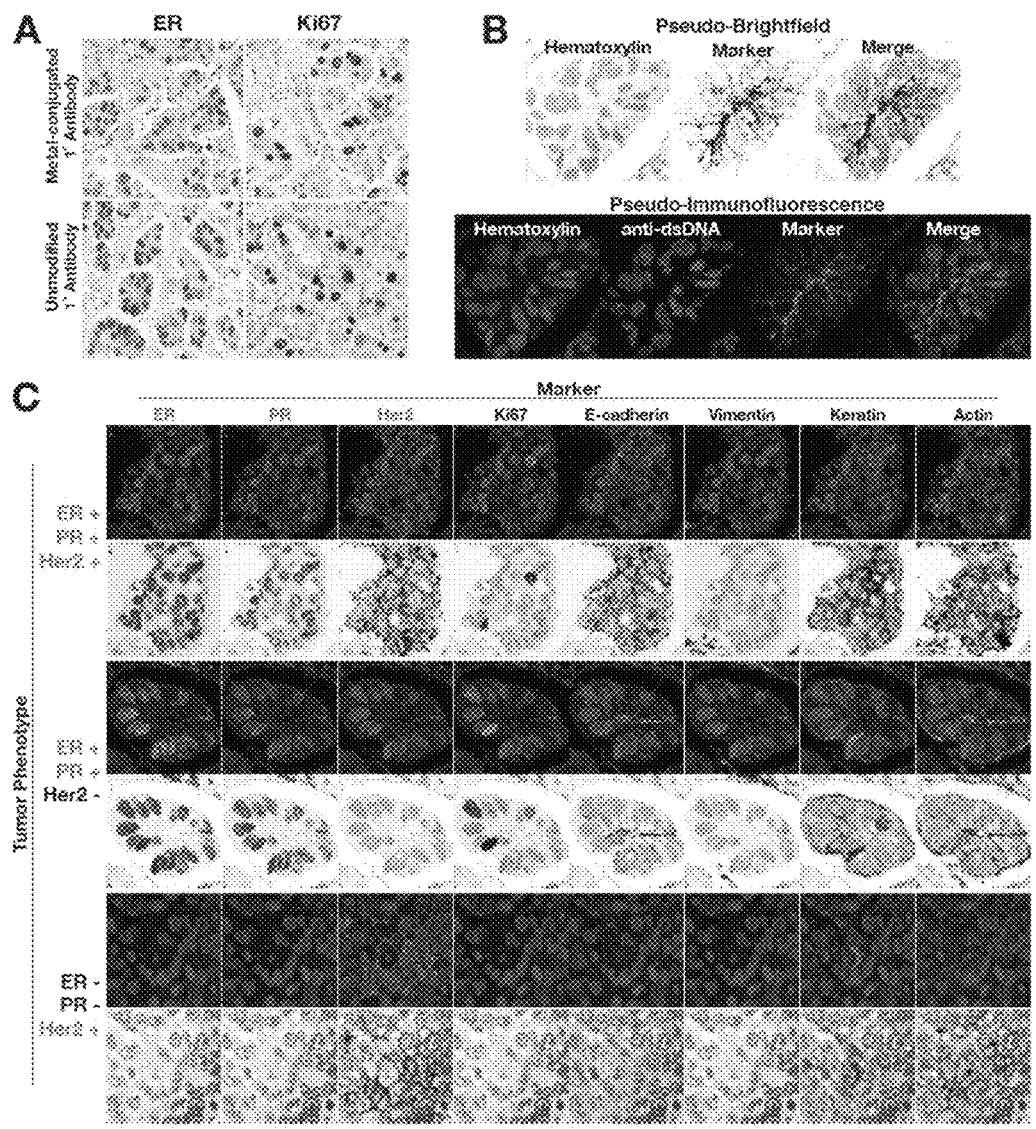
FIG. 3. 10-color imaging of human breast tumors using MIBI. (A) Avidity of is primary antibodies is unaffected by metal-conjugation. To access the effect of metal conjugation on antibody avidity, immunoperoxidase staining of serial sections from a single human breast tumor were stained with metal-conjugated or unmodified primary antibodies for Ki67 or ER-alpha. Positive-staining nuclei of comparable intensity were present in similar numbers when using metal-conjugated or unmodified primary antibodies. (B) Visual representation of MIBI data. Single channel ion data can be color mapped and merged to construct pseudo-brightfield or pseudo-darkfield images resembling conventional immunoperoxidase or immunofluorescence staining, respectively. (C) 10-color imaging of human breast tumors. FFPE tissue sections from three different patients were analyzed using MIBI. HER2, ER, and PR are expressed appropriately with respect to the known immunophenotype of each specimen. ER, PR, and Ki67 demonstrate well-demarcated nuclear positivity, while e-cadherin, actin, HER2, and keratin expression is appropriately membranous.
Figure 4:
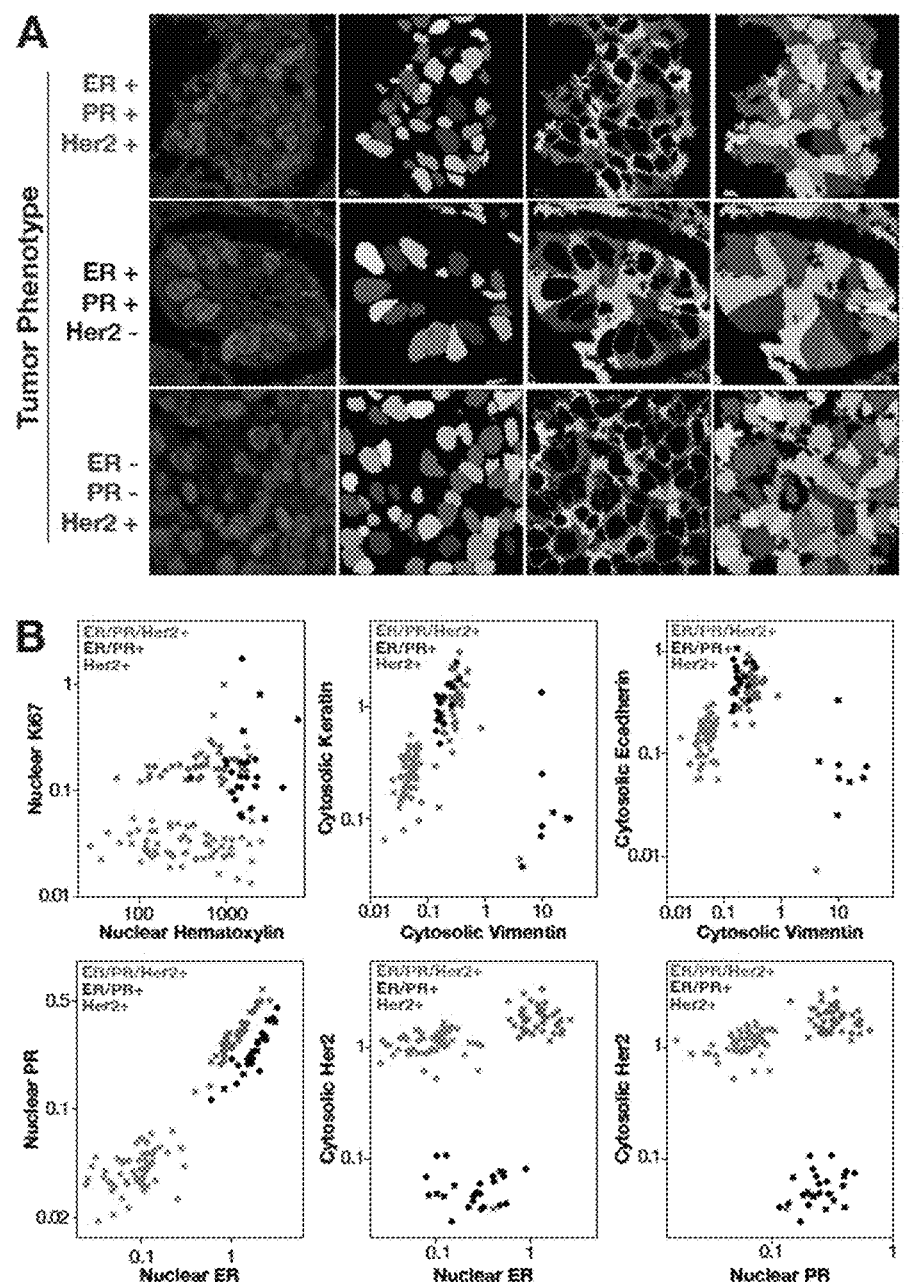
FIG. 4. Quantitative analysis of tumor immunophenotype. (A) For quantitative single cell analysis, ion images are segmented into ROIs demarcating nuclear and cytoplasmic compartments. (B) Examination of the resultant data using conventional biaxial scatter plots demonstrates quantitative expression patterns matching the known immunophenotype of each respective tumor.
Figure 5:
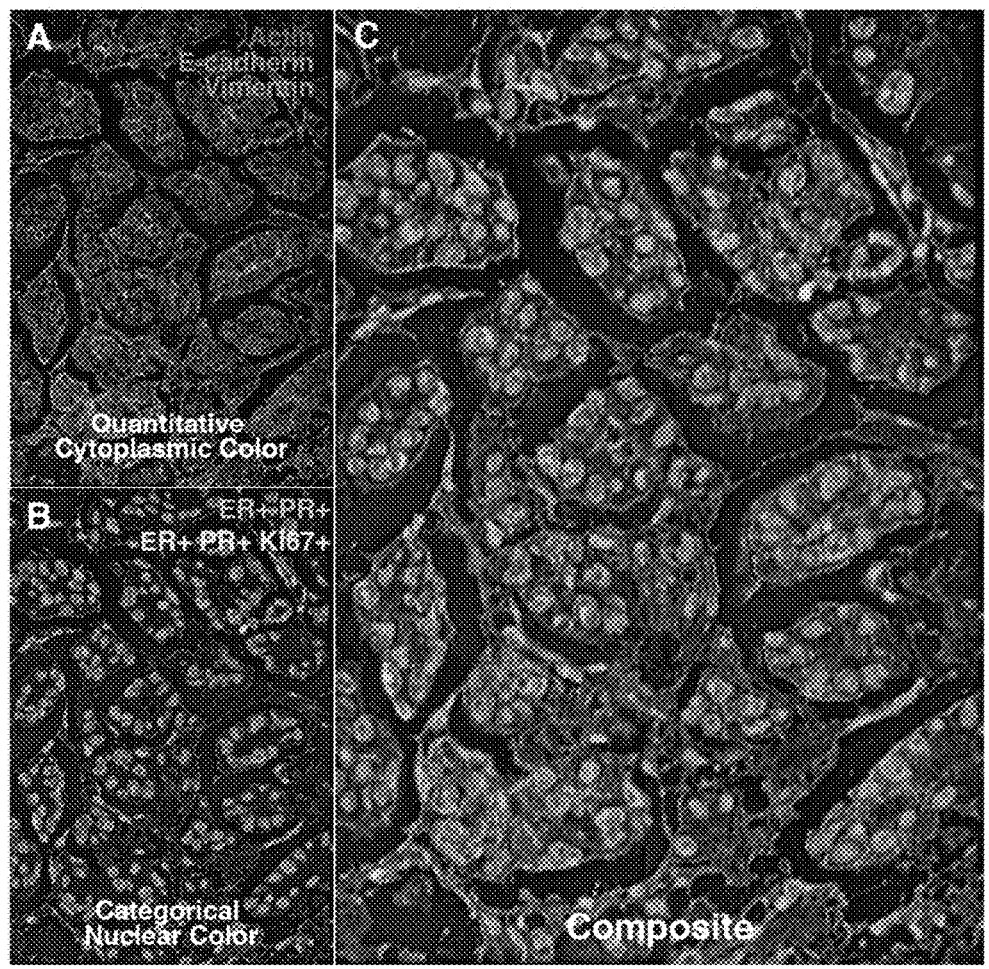
FIG. 5. Composite representation of multidimensional MIBI data using categorical and quantitative colorization. (A) Quantitative colorization of cytoplasmic features. Green-encoded e-cadherin, red-encoded actin, and blue-encoded vimentin channels were merged to generate a quantitative representation of protein expression and colocalization. (B) Categorical colorization of nuclei. Subpopulations of ER/PR/Ki67 positive or ER/PR positive nuclei are pseudo-colored yellow or aqua, respectively. (C) Multidimensional data are summarized in a composite image illustrating quantitative and categorical expression patterns.

This method circumvents some of the limitations associated with conventional light based staining methods. This method can be used on virtually any vacuum-compatible specimen, including FFPE tissue. In validating this method we were able to demonstrate an almost quantitatively identical immunophenotypic analysis of PBMCs compared to a more conventional approach (FIG. 2) as well as equivalent (staining pattern and intensity) imaging of three FFPE breast tumors with different immunophenotypes with the additional benefit of ten or more markers being analyzed simultaneously (FIG. 3). Additionally, marker multiplexing and image segmentation permitted quantitative feature extraction describing cellular and subcellular expression, that in aggregate, revealed immunophenotypes of cell subpopulations that could be related back to the original clinical pathology of the tissue (FIG. 4). Finally, novel approaches in combinatorial false coloring (or pseudo coloring) of images could distill the high dimensional analysis down to a rapidly interpretable single image where multiple phenotypes could be represented by a single color in an unsupervised fashion (FIG. 5). Such representations create an opportunity for vastly improving microscopy-based diagnostics by leveraging readily obtainable and interpretable high dimensional information using MIBI-like approaches.

MIBI has advantages over conventional IHC techniques. Background signal due to is autofluorescence is absent and the dynamic range presented here is already $10^5$, exceeding immunofluorescence and chromogenic IHC by 100-fold and 1000-fold, respectively. Because the mass resolution is less than one hundredth of a dalton, no spectral overlap is observed between different metal-conjugated primary antibodies, obviating the need for channel compensation. Assay linearity is improved relative to both chromogenic IHC and IF because neither secondary labeling nor amplified detection are required. Meanwhile, relatively conventional methods are used for immunoreactions, and because mass tags do not degrade, samples are stable indefinitely, permitting remote preparation together with a centralized reading facility.

Reagents can be developed which extends the capability of MIBI to other arenas and away from antibody-based analysis, such as in situ hybridization and subcellular metabolic analysis. Taken together, the extended capabilities of MIBI permitted by relatively minor modifications of existing analytical systems introduce the prospect of a practical, multiplexed imaging platform that integrates tissue histology, protein expression, gene expression, and metabolism on a subcellular level.

Methods

Substrate Preparation:

Silicon wafers (Silicon Valley Microelectronics) were diced into 18 mm$^2$ pieces, rinsed two times with methanol, and polished with a cotton-tipped applicator. Cleaned substrates were subsequently immersed in 2% poly-1-lysine solution (Sigma-Aldrich) for 10 min and baked at 60° C. for 1 hr.

Antibodies:

A summary of antibodies, reporter isotopes, and concentrations can be found in table S1 below. Metal conjugated primary antibodies were prepared 100 µg at a time using the MaxPAR antibody conjugation kit (DVS Sciences, Toronto, Canada) according to the manufacturer's recommended protocol. Following labeling, antibodies were diluted in Candor PBS Antibody Stabilization solution (Candor Bioscience GmbH, Wangen, Germany) to 0.4 mg/mL and stored long-term at 4° C.

TABLE S1

| Antigen | Vendor | Clone | Mass | Element |
|---|---|---|---|---|
| PBMC Primary Antibodies | | | | |
| CD45 | Biolegend | HI30 | 115 | In |
| CD19 | DVS Sciences | HIB19 | 142 | Nd |
| CD4 | DVS Sciences | RPA-T4 | 145 | Nd |
| CD14 | DVS Sciences | M5E2 | 160 | Gd |
| CD8 | Biolegend | RPA-T8 | 165 | Ho |
| CD3 | DVS Sciences | UCHT1 | 170 | Er |
| HLA-DR | DVS Sciences | L243 | 174 | Yb |
| Breast Tumor Primary Antibodies | | | | |
| ER alpha | Labvision | 1D5 | 139 | La |
| PR | Cellsignal | D8Q2J | 145 | Nd |
| Ki67 | Labvision | Polyclonal | 150 | Nd |
| Vimentin | Cellsignal | D21H3 | 154 | Sm |
| E-cadherin | Cellsignal | 24E10 | 158 | Gd |
| Pan-keratin | Cellsignal | C11 | 162 | Dy |
| Her2 | Cellsignal | D8F12 | 166 | Er |
| Pan-actin | Cellsignal | D18C11 | 168 | Er |
| dsDNA | Abcam | HYB331-01 | 176 | Yb |

Cells:

Unmatched human peripheral blood was purchased from the Stanford Blood Bank according to an IRB-approved protocol. All blood samples were collected in heparin sulfate anticoagulant, stored at room temperature for 4-6 hrs, and then separated over Ficoll-Paque Plus (Amersham Biosciences) using Accuspin tubes (Sigma-Aldrich, St. Louis, Mo.) to remove erythrocytes, platelets, and granulocytes. Cells were frozen in FCS with 10% DMSO. Cells were rested at 37° C., 5% CO2 for 1 hour in RPMI with 10% FCS (supplemented with 2 mM EDTA in the case of frozen samples), 1×L-glutamine and 1× penicillin/streptomycin (Invitrogen).

Staining of Peripheral Blood Mononuclear Cells:

Cellular staining protocols were based on procedures previously described. Briefly, after resting cells for 1 hr, surface marker antibodies were added yielding 100 µL final reaction volumes and incubated at room temperature for 30 min. Following incubation, cells were washed two times with cell staining media and split into two aliquots. For mass cytometry analysis, cells were permeabilized with 4° C. methanol for 10 min at 4° C., washed twice with cell staining media to remove residual methanol, and then stained with 1 mL of 1:4000 191/193Ir DNA intercalator diluted in PBS with 1.6% PFA for 20 mins at room temperature. Cells were then washed once with cell is staining media, once with PBS, and then diluted in dH2O to approximately 106 cells/mL prior to analysis. For MIBI analysis, 50 µL of cells diluted in PBS to approximately $10^7$ cells/mL were placed on silicon substrate and allowed to adhere for 20 min. The substrate was then gently rinsed with PBS, fixed for 5 min in PBS with 2% glutaraldehyde, and rinsed twice with dH2O. Lastly, samples were dehydrated via a graded ethanol series, air dried at room temperature, and stored in a vacuum desiccator for at least 24 hrs prior to analysis.

Breast Tumor Tissue Sections:

Tissue sections (4 µm thickness) were cut from FFPE tissue blocks of human breast tumor using a microtome, mounted on poly-1-lysine-coated silicon substrate for MIBI analysis or a glass slide for immunoperoxidase (IPDX) staining. Silicon-mounted sections were baked at 65° C. for 15 min, deparaffinized in xylene, and rehydrated via a graded ethanol series. The sections were then immersed in epitope retrieval buffer (10 mM sodium citrate, pH 6) and placed in a pressure cooker for 30 min (Electron Microscopy Sciences, Hatfield, Pa.). The sections were subsequently rinsed twice with dH$_2$O and once with wash buffer (TBS, 0.1% Tween, pH 7.2). Residual buffer was removed by gently touching the surface with a lint-free tissue prior to incubating with blocking buffer for 30 min (TBS, 0.1% Tween, 3% BSA, 10% donkey serum, pH 7.2). Blocking buffer was subsequently removed and the sections were stained overnight at 4° C. in a humidified chamber. The following morning, the sections were rinsed twice in wash buffer, postfixed for 5 min (PBS, 2% glutaraldehyde), rinsed in dH$_2$O, and stained with Harris hematoxylin for 10 s. Finally, the sections were dehydrated via graded ethanol series, air dried at room temperature, and then stored in a vacuum desiccator for at least 24 hrs prior to imaging. Antigen retrieval was performed using a Decloaking Chamber (Biocare Medical, Concord, Calif.) with citrate buffer at pH 6.0, 125° C. and pressure to 15 psi. The total time slides were in the chamber was 45 min. Incubations with primary antibodies were performed at room temperature overnight in a humidified chamber. Normal goat serum was used for blocking. Biotinylated goat anti-rabbit (1:1000) was the secondary antibody used with a Vectastain ABC Kit Elite and a Peroxidase Substrate Kit DAB (Vector Labs, Burlingame, Calif.) used for amplification and visualization of signal, respectively. Tissues known to contain each assessed antigen were used as positive controls.

MIBI Analysis:

MIBI analysis was performed with a NanoSIMS 50 L mass spectrometer (Cameca) using an O-primary ion beam supplied by an oxygen duoplasmatron source. The primary optics, secondary optics, and mass spectrometer were tuned prior to each experiment. The seven detector trolleys were calibrated using metal conjugated antibody standards implanted on silicon. The detector trolleys were first moved along the focal plane to the mass peak of the metal corresponding to each antibody. Mass peaks were then centered on the detectors by performing high mass resolution (HMR) scans and adjusting the deflector voltage of each trolley. Horizontal and vertical beam alignment was tuned to maximize secondary ion transmission through the entrance slit of the mass spectrometer. Then, the z-position of the sample stage was adjusted such that the secondary ion signal was maximal when the voltage of the third electrode of the immersion lens (E0S) was approximately 7150 V. The primary ion beam was centered on the region of interest (ROI) by tuning lenses Lduo, L0, and L1. All data were taken in positive ion mode using D1 aperture 2, D0 aperture 0 or 3, L1 voltage of approximately 1500 V, entrance slit 0, and aperture slit 0. Images containing more than seven channels were acquired by recalibrating the detector trolleys between repeat scans of the same field. ROIs identified on serial sections using brightfield microscopy were located using the CCD camera in the NanoSIMS analysis chamber. Samples were implanted with O— at high primary ion current until the secondary ion yield had reached steady state. The Oct-90 and Oct-45 voltages of the stigmator octopole were manually adjusted to minimize image distortion while viewing a realtime ion image (RTI) of a periodic aluminum grid. Prior to each image acquisition, the field of view was manually focused by adjusting the voltage of the second electrode of the immersion lens (EOP) while viewing a RTI. Ion images were acquired over a 50-100 µm fields of view with pixel dwell times between 2-10 ms and up to 10 repeat scans over a single area. Total scan time for a single field of view ranged between 5-25 min. Larger areas were constructed by stitching together multiple contiguous fields of view into a single mosaic.

Mass Cytometry Measurement:

Cell events were collected on a CyTOF mass cytometer as previously described. With detection in dual counting mode using the 'data' calibration, cell length was set to range from 10 to 75 with a convolution threshold of 100. A is detector stability delay of 20 seconds was used and all samples were diluted such that the acquisition rate was less than 500 cells per second.

PBMC Mosaic Stitching:

The MIBI PBMC data was collected in a series of 1200 individual square 50 µm (128 pixel) tiles, arranged in a 40×30 rectangle. The relative positions of the tiles were determined using the log-transformed CD45 images. The reported offset between adjacent tiles was 40 µm in both the x- and y-directions, but the actual offset was observed to vary due to imprecision in the stage's location. To account for this, each tile was initially placed according to its reported offset, and then moved around 1-20 pixels in both the x- and y-directions to multiple different positions. At each location, the correlation in the overlap area between the new tile and previous tile was computed. The tile was then assigned to the position that maximized the correlation of the overlapped areas.

PBMC Image Segmentation:

The log-transformed mosaic of CD45 tiles was convolved with a 2-dimensional Gaussian kernel with standard deviation of 3 pixels, and then thresholded at a density of 1. Each continuous region with density greater than this threshold was preliminarily labeled as an individual cell. The next step was to separate into their constituent singlets any sets of multiple cells that were close enough to be initially labeled as single cells. To do this, for each preliminary cell, the two points on the boundary were identified between which there was the maximum ratio of distance along the boundary to Euclidean distance (the "pinch points"). When this ratio exceeded 0.42 (a heuristic cutoff), the preliminary cell was separated into two cells with a new border segment between the pinch points. This process was iterated over all cells, and repeated with each new preliminary cell created, until no cells had pinch points that exceeded this separation criteria.

Once the cell boundaries were determined, the raw values of each channel measured were summed within each boundary to create a table of total ion intensity on a per-cell basis. The number of pixels within each cell was also calculated as a measure of cell size. This table was equivalent to an .fcs file such as from a standard mass cytometry experiment.

Data Analysis:

To filter out doublets and debris, singlets were gated from the mass cytometry PBMCs by applying standard cell-length by DNA and then cell-length by CD45 gates; a singlet gate using cell area by CD45 was applied to the MIBI PBMCs. The subsequent is gating scheme for both the MIBI and CyTOF processed PBMCs is shown in FIGS. 2B and C, respectively.

Results

Performance Assessment of MIBI:

The workflow for MIBI is comparable to immunofluorescence (IF) and chromogenic IHC assays (FIG. 1). Instead of fluorophores or enzyme-conjugated reagents, biological specimens are incubated with primary antibodies coupled to isotopically pure, stable lanthanides (FIG. 1). Primary antibodies are combined in solution for simultaneous incubation with the specimen. The specimens prepared for MIBI are mounted in a sample holder and subjected to a rasterized oxygen duoplasmatron primary ion beam. The impact of this ion beam on the sample liberates lanthanide adducts of the bound antibodies as secondary ions. In this study, the secondary ions are subsequently analyzed via a magnetic sector mass spectrometer equipped with multiple photomultiplier tubes, permitting parallel detection of multiple lanthanide isotopes (mass-based reporters). The resultant data produces a two-dimensional map of the elemental distribution of each lanthanide, and thus each antibody and its corresponding epitope.

Figure 2:
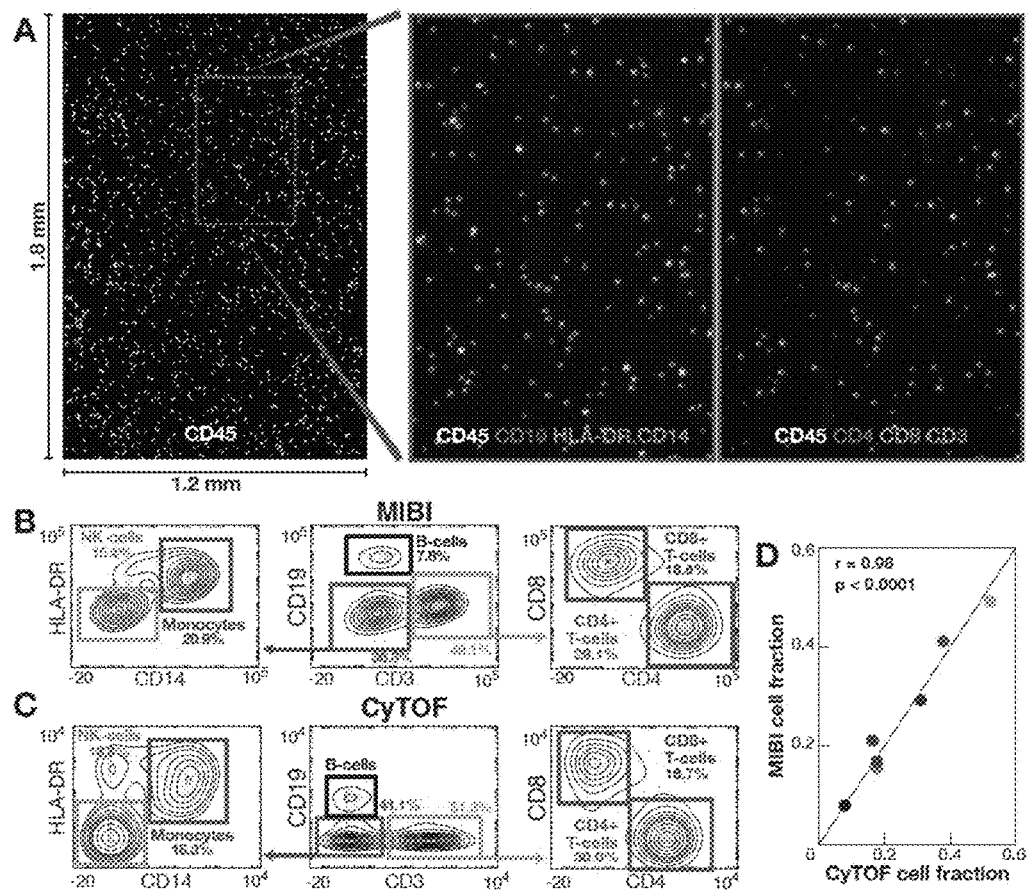
FIG. 2. Analysis of PBMCs stained with metal-conjugated antibodies using mass cytometry and MIBI. (A) PBMCs stained with seven antibodies were immobilized on a silicon wafer and imaged using MIBI. Single cell regions of interest were segmented using CD45 surface expression and integrated for each antibody. (B, C) Hierarchical gating of the resultant data yielded comparable values for seven cell populations relative to those found by mass cytometry. (D) Pearson correlation of the relative abundance of each cell population demonstrated strong agreement between the two methods (r=0.98, p<0.0001, two-tailed t test).

Peripheral blood mononuclear cells (PBMC) stained with seven metal isotopeconjugated primary antibodies (CD3, CD4, CD8, CD14, CD19, CD45, HLA-DR) were assessed in parallel using mass cytometry and MIBI (FIG. 2). Mass cytometry was performed on the PBMC suspension as described previously. For MIBI, cells were immobilized on a poly-1-lysine-coated silicon wafer, dried under vacuum, and subsequently analyzed using a NanoSIMS 50L™ mass spectrometer. Sequential 50-m fields were imaged and constructed into a composite mosaic for each antibody (FIG. 2A). The resultant mosaic was segmented into single-cell regions of interest (ROIs) using the CD45 channel. To extract single cell expression data for each antibody, the ion count for each channel was integrated for each cell ROI.

Mass cytometry and MIBI produced comparable results and qualitative patterns of expression when analyzed via traditional biaxial plots (FIG. 2B) with marker intensity of MIBI having a dynamic range of 105. Additionally, both platforms yielded quantitatively similar frequencies for seven manually gated cell populations (FIG. 2C), with three of these is populations differing by less than 1% between platforms (B-cells, CD8+ T-cells, CD4+ T-cells). Altogether, using PBMCs as a test case, MIBI could yield both qualitatively and quantitatively equivalent results as a conventional analytical platform with the additional benefit of spatial information.

Ten-Color Imaging of Human Breast Tumor Tissue Sections:

In order to utilize MIBI for analysis of tissue sections acquired in a diagnostic setting, we sought to verify the activity of metal-conjugated reagents used in conventional IHC staining by comparing metal-conjugated and unmodified primary antibodies. Secondary staining of serial sections from a single FFPE human breast tumor tissue block treated with metal-conjugated or unmodified primary antibodies for Ki67 or estrogen receptor alpha (ER) demonstrate positive nuclear staining of comparable intensity and similar levels of background staining (FIG. 3A), indicating that the metal conjugation did not materially affect specific and non-specific staining behavior.

Finally, to assess the overall performance of MIBI in a diagnostic imaging application FFPE breast tumor tissue sections from three different patients were analyzed. ER, progesterone receptor (PR), and HER2 positivity were verified in a clinical IHC lab using validated reagents. For MIBI, tumor sections were mounted on poly-1-lysine-coated silicon wafers, deparaffinized, and subjected to heat-induced epitope retrieval prior to overnight staining with metal-conjugated antibodies for dsDNA, ER, progesterone receptor (PR), e-cadherin, Ki67, vimentin, actin, keratin, and HER2. Conveniently, a hematoxylin counterstain can be readily detected by measuring its elemental aluminum content. The following day the sections were washed, counterstained with hematoxylin, and dehydrated via graded ethanol series.

Using the MIBI analysis, conventional high resolution images can be constructed of FFPE tissues. Pseudo-brightfield images mimicking traditional DAB staining were constructed by encoding hematoxylin on a white to blue scale while putting the desired marker on a white to brown scale (FIG. 3B, top). Pseudo-fluorescence images mimicking three-color immunofluorescence were constructed using a red-encoded dsDNA channel, a blue-encoded hematoxylin channel, and a green encoded marker channel (FIG. 3B, bottom). Pseudo-brightfield and pseudo-fluorescence composites for each antibody within a single field of view is are shown for each of the three tissue sections in FIG. 3C. Comparison of HER2, ER, and PR positivity across the three specimens demonstrates appropriate expression with respect to immunophenotypes established by conventional IHC staining. Sections expressing ER and PR demonstrate well-demarcated nuclear staining, scattered Ki67-positive nuclei, and intense positive staining for vimentin in mesenchymal cells. HER2-positive sections demonstrate strong membrane staining. Ecadherin, actin, and keratin also demonstrate appropriate subcellular staining patterns.

Image Segmentation and Feature Extraction from Simultaneously Acquired Markers:

In order to fully leverage the nature of the information inherent in the quantitatively multiplexed images in this study, image segmentation was performed so that cellular features could be analyzed and compared. Hematoxylin and dsDNA channels for each tumor were segmented using CellProfiler in order to extract summary statistics describing subcellular expression (FIG. 4A). Mean pixel intensities were quantified for each marker within nuclear cytoplasmic, and cellular ROIs for each cell. Biaxial scatter plots demonstrate marker coexpression matching the known immunophenotype for each tumor (FIG. 4B). Triple-positive and ER-PR doublepositive tumors demonstrate nuclear co-expression of ER and PR that is absent in the HER2-positive tumor. Triple-positive and HER2-positive tumors demonstrate cytoplasmic HER2-positivity that is absent in the ER-PR double-positive tumor. Subpopulations of keratin, e-cadherin-positive ductal cells are distinctly segregated from vimentin-positive mesenchymal cells.

Integrated histological and immunophenotypic features of multidimensional MIBI data can be visualized by generating composite images that combine quantitative (continuous) cytoplasmic and categorical (positive or negative) nuclear expression patterns (FIG. 5). Hormone-receptor-positive regions within the epithelial compartment, showing variable non-nuclear expression of actin (red) and e-cadherin (green), can be distinguished from interspersed mesenchymal cells co-expressing actin (red) and vimentin (blue). Approximately 8% of cells are seen to be Ki67-positive. Unlike conventional chromogenic IHC, which is not well-suited to detecting colocalization of multiple markers, MIBI analysis readily demonstrates ER-PR doublepositive (aqua) or ER—PR-Ki67 triple-positive (yellow) subpopulations. In this instance, low-abundance proliferating cell populations co-expressed ER is and PR. It is conceivable that detailed, cell-by-cell, analysis of molecular phenotypes, especially if multiple nuclear antigen expression profiles are queried, may prove to have practical clinical significance, identifying subsets of malignant cells that may have different responses to therapy than the bulk tumor population. These observations, combined with the quantitative dynamic range of mass spectrometry approaches like MIBI lends itself to potential diagnostic applications where such co-localizations and interactions may now be identified in an unsupervised fashion.

What is claimed is:

1. A method of generating a high resolution two-dimensional image of a tissue sample comprising cells and extracellular structures, the method comprising:
    labeling a tissue section with a plurality of distinguishable elemental isotopic mass tags, thereby producing a labeled tissue section in which biological features are bound to the elemental isotopic mass tags;
    scanning a plurality of positions across an area of the labeled tissue section with a secondary ion mass spectrometer (SIMS) ion beam to, at each position, simultaneously measure the plurality of elemental isotopic mass tags, to thereby generate a data set that comprises identity and spatially-addressable measurements of the abundance of each of the plurality of elemental isotopic mass tags at each of the plurality of positions in the tissue section; and
    outputting an image of the tissue section showing the biological features therein.

2. The method of claim 1, wherein said labeling is done using antibodies that are linked to the elemental isotopic mass tags.

3. The method of claim 1, wherein the tissue section is a formalin-fixed, paraffin-embedded (FFPE) section.

4. The method of claim 1, wherein said elemental isotopic mass tags are isotopes of elements having an atomic number in the range of 21-92.

5. The method of claim 4, wherein each element is a lanthanide.

6. The method of claim 1, wherein the image has a resolution of at least 500 nm.

7. The method of claim 1, further comprising defining the boundaries of individual cells, and, optionally, subcellular features in individual cells, in said image.

8. The method of claim 7, further comprising integrating the data set that corresponds to each of the individual cells, or a subcellular feature thereof, in said image.

9. The method of claim 8, further comprising categorizing said cells based on the integrated data obtained for each of the cells or a subcellular feature thereof.

10. The method of claim 9, further comprising displaying the image of said tissue section, wherein the cells are color-coded by their category.

11. The method of claim 10, wherein, in any one pixel of the image, intensity of a color of said pixel correlates with magnitude of a signal obtained for that pixel by said scanning.

12. The method of claim 1, wherein said tissue section is mounted on a conductive substrate.

13. The method of claim 1, wherein said ion beam is rastered over said tissue section.

14. A system for analyzing a tissue sample comprising cells, the system comprising:
   a) a secondary ion mass spectrometry (SIMS) system comprising a holder for retaining a substrate comprising a tissue section, wherein the system is configured to (i) scan a plurality of positions across an area of the tissue section with a SIMS ion beam to, at each position, simultaneously measure a plurality of elemental isotopic mass tags that are bound to biological features in the tissue section, (ii) generate a data set that comprises the identity and spatially-addressable measurements of the abundance of each of the plurality of elemental isotopic mass tags at the plurality of positions across the area of said tissue section, and (iii) output the data set; and
   b) a computer comprising an image analysis module that processes said data set to produce an image of said tissue section.

15. The system of claim 14, wherein said image analysis module can define the boundaries of individual cells, and, optionally, subcellular features in individual cells, in said image.

16. The system of claim 15, wherein said image analysis module integrates the data set for individual cells in the image or a subcellular feature thereof.

17. The system of claim 16, wherein said image analysis module categorizes said individual cells based on the integrated data obtained for each of the cells.

18. The system of claim 17, wherein said image analysis module displays an image of said tissue section, wherein the cells are color-coded by their category.

19. The system of claim 18, wherein, in any one pixel of the image, the intensity of color of said pixel correlates with magnitude of a signal obtained for that pixel by the SIMS system.

* * * * *

UNITED STATES PATENT AND TRADEMARK OFFICE
CERTIFICATE OF CORRECTION

PATENT NO. : 10,041,949 B2
APPLICATION NO. : 14/483999
DATED : August 7, 2018
INVENTOR(S) : Sean C. Bendall et al.

Page 1 of 1

It is certified that error appears in the above-identified patent and that said Letters Patent is hereby corrected as shown below:

In the Specification

In Column 1, Lines 14-18: Please delete the paragraph starting with "This invention" ending with "in the invention." and replace it with the following paragraph:
-- This invention was made with Government support under contracts AI057229, CA034233, CA130826, EY018228, GM104148, and HHSN272200700038C awarded by the National Institutes of Health. The Government has certain rights in the invention. --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*